US009759692B2

(12) United States Patent
St-Laurent et al.

(10) Patent No.: US 9,759,692 B2
(45) Date of Patent: Sep. 12, 2017

(54) SYSTEM AND METHOD OF DYNAMIC GATING IN NON-DESTRUCTIVE WELD INSPECTION

(71) Applicants: Martin St-Laurent, Quebec (CA); Benoit Lepage, Ancienne-Lorette (CA)

(72) Inventors: Martin St-Laurent, Quebec (CA); Benoit Lepage, Ancienne-Lorette (CA)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 252 days.

(21) Appl. No.: 14/722,501

(22) Filed: May 27, 2015

(65) Prior Publication Data
US 2015/0346164 A1    Dec. 3, 2015

Related U.S. Application Data

(60) Provisional application No. 62/005,358, filed on May 30, 2014.

(51) Int. Cl.
*G01N 29/26*    (2006.01)
*G01N 29/32*    (2006.01)
(Continued)

(52) U.S. Cl.
CPC ....... *G01N 29/4463* (2013.01); *G01N 29/043* (2013.01); *G01N 29/24* (2013.01);
(Continued)

(58) Field of Classification Search
CPC .. G01N 29/4463; G01N 29/043; G01N 29/24; G01N 2291/044; G01N 2291/267; G01N 2291/0234
(Continued)

(56) References Cited

U.S. PATENT DOCUMENTS 5,677,490 A * 10/1997 Gunther ............... G01N 29/043
73/620
6,951,540 B2 * 10/2005 Ebbini ................ G01S 7/52039
600/437
(Continued)

OTHER PUBLICATIONS

American Society of Mechanical Engineers 2005 article "Pipeline Girth Weld Inspection using Ultrasonic Phased Arrays" (by Michael Moles, Noel Dubé, Simon Labbé, and Ed Ginzel), published in the US.
2011 ASTM E-1961-11 publication "Standard Practice for Mechanized Ultrasonic Testing of Girth Welds Using Zonal Discrimination with Focused Search Units.", published in West Conshohocken, PA, US.

*Primary Examiner* — J M Saint Surin
(74) *Attorney, Agent, or Firm* — C. Tricia Liu

(57) ABSTRACT

A phased array ultrasonic inspection system configured for weld inspection includes a data analysis process with automated and optimized gating to take into account the actual distance between a phased array probe and a weld line. The system embodies a weld tracking module and a dynamic gating module. The tracking module produces dynamically corrected overlays of the weld line based on the echo signals, the dynamically corrected overlays having a series of offsets from the corresponding initial overlays. The dynamic gating module purposefully positions a plurality of data analysis gates to filter out noise signals caused by sources unrelated to the weld, and to provide dynamic target gating adjusted by at least part of the offset.

21 Claims, 8 Drawing Sheets

(51) Int. Cl.
*G01N 29/24* (2006.01)
*G01N 29/04* (2006.01)
*G01N 29/44* (2006.01)
*G01N 29/265* (2006.01)

(52) U.S. Cl.
CPC ......... *G01N 29/262* (2013.01); *G01N 29/265* (2013.01); *G01N 29/32* (2013.01); *G01N 2291/0234* (2013.01); *G01N 2291/044* (2013.01); *G01N 2291/267* (2013.01); *G01N 2291/2675* (2013.01)

(58) Field of Classification Search
USPC .......................................................... 73/588
See application file for complete search history.

(56) References Cited

U.S. PATENT DOCUMENTS

| | | | | |
|---|---|---|---|---|
| 8,365,602 | B2 | 2/2013 | Imbert et al. | |
| 9,032,802 | B2* | 5/2015 | Imbert | G01N 29/27 73/622 |
| 9,037,419 | B2* | 5/2015 | Na | G01N 29/0645 702/39 |
| 9,492,139 | B2* | 11/2016 | Rosen | A61B 8/08 |
| 2001/0052264 | A1* | 12/2001 | Johnson | B23K 31/125 73/628 |
| 2008/0271537 | A1* | 11/2008 | Panyard | G01N 29/225 73/629 |

* cited by examiner

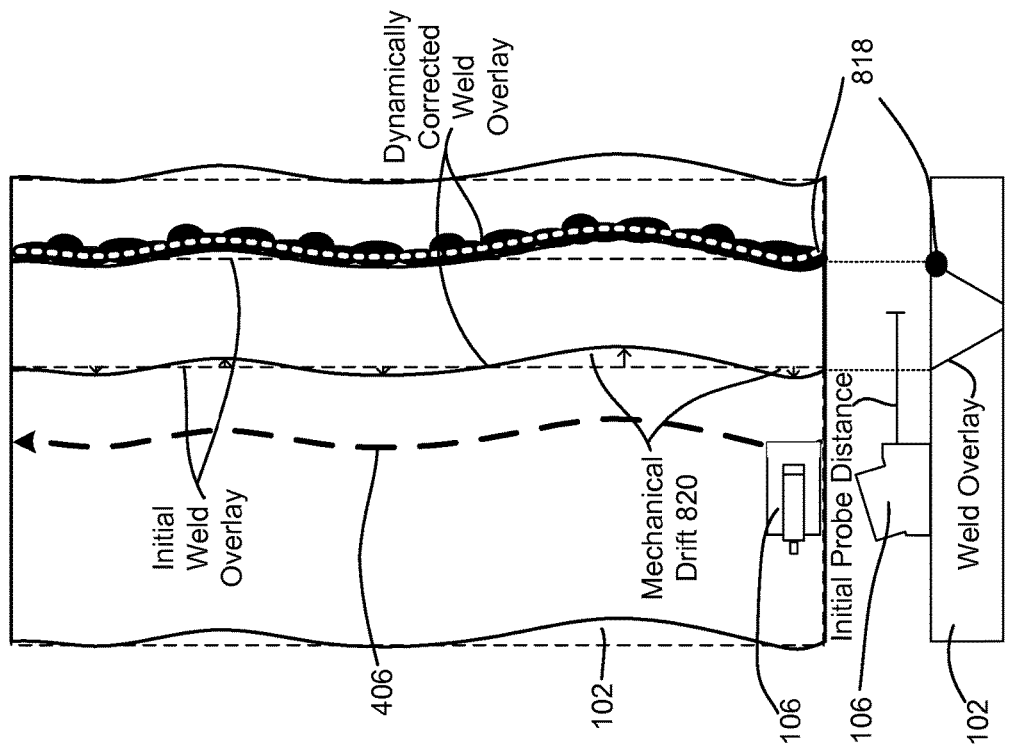
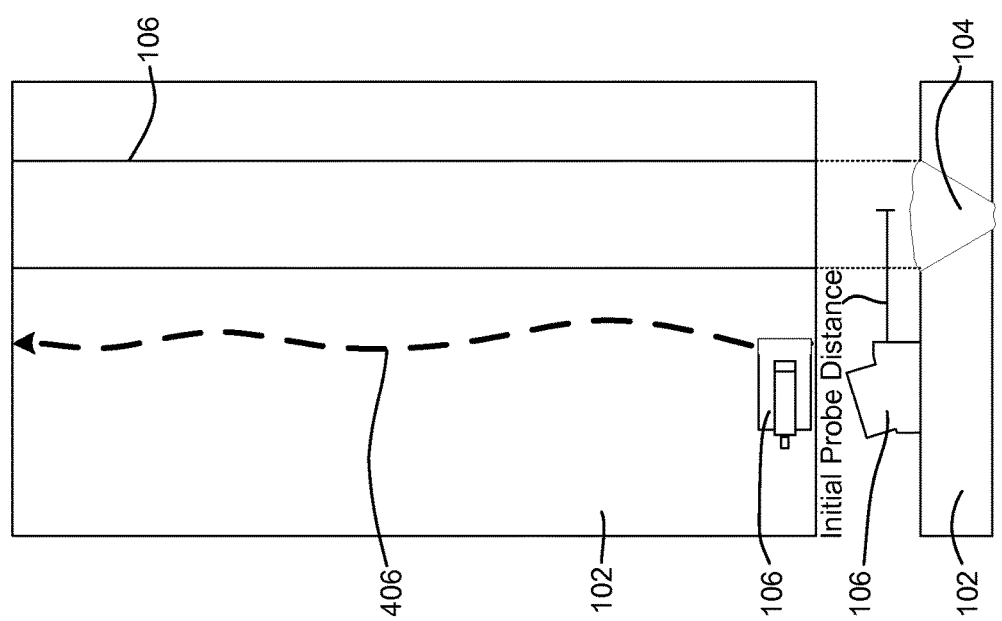

SYSTEM AND METHOD OF DYNAMIC GATING IN NON-DESTRUCTIVE WELD INSPECTION

CROSS-REFERENCE TO RELATED APPLICATIONS

This application claims the benefit and priority of U.S. Provisional patent application Ser. No. 62/005,358 filed May 30, 2014 entitled A SYSTEM AND METHOD OF DYNAMIC GATING IN NON-DESTRUCTIVE WELD INSPECTION, the entire disclosure of which is incorporated herein by reference.

FIELD OF THE INVENTION

The present disclosure generally relates to a method and a system for conducting non-destructive testing/inspection (later as NDT/NDI), and more particularly to positioning data interpretation aids with dynamic gating guided by the response signals obtained either during a phased array ultrasonic inspection or post inspection.

BACKGROUND OF THE INVENTION

Phased array ultrasonic testing (PAUT) is an advanced method of ultrasonic testing (UT) that has applications in industrial nondestructive testing. Common applications are to find flaws in manufactured materials such as welds.

Single-element (non-phased array) probes, known technically as monolithic probes, emit a beam in a fixed direction. To test a large volume of material, a conventional probe must be physically moved or turned to sweep or scan the beam through the area of interest.

In contrast, the beam from a PAUT probe can be moved electronically, without moving the probe, and can be swept through a wide volume of material at high speed. The beam is controllable because a PAUT probe is made up of multiple small elements, each of which can be pulsed individually at a computer-calculated timing. The term phased refers to the timing, and the term array refers to the multiple elements. The elements of the probe that contribute to beam formation is defined as the aperture of the beam; the aperture can include a portion or all of the elements of the PAUT probe.

During typical inspections of welds, multiple beams are generated from a single or multiple apertures at various incidence angles. These generate an image showing reflections (or diffractions) of the ultrasonic waves that are associated with defects within the part over the scanned weld's areas of interest (where defects are expected to be found). For cases where the aperture is fixed and only angles are changed, the image is called a sectorial scan or s-scan.

In order to have an appropriate coverage of the weld area, it is almost always required to combine inspection from both sides of the weld. For defining the inspection, standards and normalized practice cover the guidelines for defining the probe and beam configuration, an example being the Non-destructive Examination (Section V) Boiler and Pressure Code of American Society of Mechanical Engineers. A weld inspection typically involves the use of a wedge, which defines a first mechanical incidence angle to generate an s-scan with shear waves in the 40 to 70 degree range of refraction angle, and a mechanical scan of the weld by moving the probe arrangement parallel to the weld axis.

A recurring problem associated with weld inspection with phased array ultrasonic scans is discrimination of relevant indications from acoustic reflections within the wedge, various ultrasonic paths involving mode conversion, or reflection from the weld geometry itself (referred to as geometric echoes).

FIG. 1a shows some typical problems with various positions that could be used for the inspection of a weld 104 in a flat part 102 using phased array probes 106a and 106b. Doing an NDI ultrasonic inspection, the inspector usually targets specific areas of the part 102 to be screened for defects. However, the sound has to travel a distance in the part 102 that does not need to be screened, for example the first leg of an ultrasonic beam 108.

Noise echoes from a flaw 112, for example, can become detrimental in the PAUT inspection. Most of the time these noise echoes will appear in areas that are not relevant for the weld inspection. To improve the signal to noise ratio (SNR), it is a common practice that inspectors define gates to select which section of the signal they want to keep. (Signals outside of the gates are discarded from the top/side view representation). Several types of gates can be placed to select a certain section along either the ultrasonic beam 108, a range of depth in the part, or, in the present disclosure, 2D polygons 120 and 122 on the weld cross section, which are referred to here as 2D gates.

One example of 2D gating is that gate 120 is used to screen the whole section of weld 104 to enable analysis of all signals coming from the weld, but discarding the noise echo from flaw 112. The 2D gate 122 used to screen only the fusion section of the weld to analyze an indication 118, but discarding noise echo from flaw 112. Another 2D gate can be used to screen only the toe crack section of the weld to enable analysis of a defect but discarding noise echo from flaw 112, or screen only the body of the weld to analyze porosity but discarding noise echo from flaw 112.

Continuing with FIG. 1a, 2D gates permit selection of a signal in relation to the real origin of the signals associated with ultrasonic beam 108 in part 102; this is the most effective gating process for improving the signal to noise ratio. Selecting that signal discards noise echo from flaw 112, and keeps the valid indication 118 for analysis. This type of gate can also be used to help identify defect types that are occurring in a particular section of weld 104. The main output of the 2D gates are top and/or side views using a color or grayscale palette, on which the noise signal is filtered to retain information relevant only to the inspection of 2D gates 120 and 122.

FIG. 1b is a schematic view of an example scan using a simplified representation of a manual scanner 404 linking the two phased array probes 106a and 106b. Each probe is placed on part 102 on each side of the weld 104. The scanner is then moved along the weld in a motion represented by a scan path 406 and a scan path 408. As can be seen, the paths are not perfectly straight, and they drift to the left and to the right causing mechanical drift from the weld.

Both the scan paths 406 and 408 are identical, but shifted along the weld depending on the probe position. It would be desirable for the probes to have coherent gating and tracking that automatically adjusts the position of the flaw indications in relation to the weld, so that information from multiple probes can be correlated.

Such concepts in FIGS. 1a and 1b, in particular the use of 2D gates, require good precision in positioning the probe relative to the weld, and keeping that relative distance constant over all the acquisition. This is difficult to achieve with an automated system, and even more so when doing a manual scan where drift is inevitable.

Part overlay is a known concept in many domains of existing practice in the field of NDT/NDI, including NDI data analysis, as it helps the inspector visualize the relative position of flaw indications in relation to the weld geometry. In order to conduct the analysis of the PAUT signals, it is typical current practice to manually adjust the probe-to-weld distance to fit echoes on a PAUT view that illustrate signals in the weld cross section, and which are related to the geometry of the part on the weld overlay One of the objectives of the present disclosure to automate this data analysis operation for all positions of the scan.

A solution for this problem has been found in automated girth weld inspection through use of the zone discrimination technique. The use of PAUT for inspection of pipeline girth weld has been described in various publications such as the American Society of Mechanical Engineers 2005 article "Pipeline Girth Weld Inspection using Ultrasonic Phased Arrays" (by Michael Moles, Noel Dubé, Simon Labbé, and Ed Ginzel), and incorporated in industrial standard practice such as the 2011 ASTM E-1961-11 publication "Standard Practice for Mechanized Ultrasonic Testing of Girth Welds Using Zonal Discrimination with Focused Search Units." In practice, the technique involves a precise gating of the signals at specific zones where defects are expected. The downside of this method is the very high precision level required for positioning the probe relative to the weld, which makes the method suitable only for high precision automated inspection.

Another solution is to conduct a thorough analysis of the data acquired during the inspection by investigating each and every indication reported in the inspected part thickness range, by using depth related gates. While this method has been adapted for manual inspection, it is also time consuming and operator dependent.

Some automatic weld tracking methods are used in existing practice, such as U.S. Pat. No. 8,365,602, but they typically require direct access to the weld area. They require additional probes located on the top of the weld, and are typically suitable only for regular and predictable weld processes.

It would be therefore be desirable to have a method allowing precise gating of the ultrasonic signal for the inspection of a weld without the use of a precise positioning scanner.

It would also be desirable for this method to be as independent of the operator as possible.

It would also be desirable for this method to use only the existing or required hardware, with no extra dedicated tracking probe or other external device.

It would also be desirable for this method to be applicable to relatively harsh welding conditions.

SUMMARY OF THE INVENTION

Disclosed is a guide system and method to aid inspecting a weld by ultrasonic phased array NDT. In the exemplary embodiment, the guide system assists the inspection of a plate-V-groove butt weld using a phased array ultrasound technique. Preferably, an initial probe is set along the weld center line using an existing automated configuration assistant based on known geometric parameters of the part. An acquisition unit of the phased array system is configured according to these parameters, and is ready to inspect.

The guide system embodies an NDI data acquisition unit comprising an ultrasonic phased array probe that is connected to a software module. The software module analyzes a PAUT signal to determine its geometrical echo position, and provides that information to a display unit and a post-data acquisition unit. The post-data acquisition unit records the tracking information of the PAUT signal in a tracking module for a later tracking analysis. A gating module can use the results from the tracking module to apply a precise placement of the probe's position in relation to the weld.

The display unit shows an overlay of the part in addition to the acquired data, which is positioned according to the software module's data analysis; this can be done as a live aid during inspection, or used for a post inspection analysis. It can make use of a position encoder, but does not have to depend on the use of such.

The novel aspects of the present disclosure can be summarized to include: an image tracking algorithm to position data interpretation as a part/weld drawing directly on the scan data; and use of the said position data to apply a volume coherent gate on the scan data, and to produce a targeted PAUT display that has a better signal to noise ratio.

BRIEF DESCRIPTION OF THE DRAWINGS

FIGS. 5a and 5b are schematic top views of an exemplary scan with the geometrical echo tracking module and a resulting weld overlay.

DETAILED DESCRIPTION OF THE INVENTION

Figure 1A:
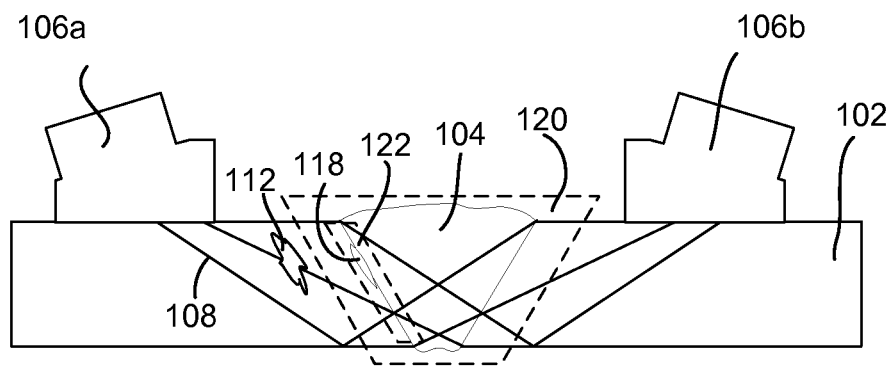
FIGS. 1a and 1b (Prior Art) are schematic views showing recurring measurement problems in existing practice associated with weld inspection using phased array ultrasonic scans.
Figure 1B:
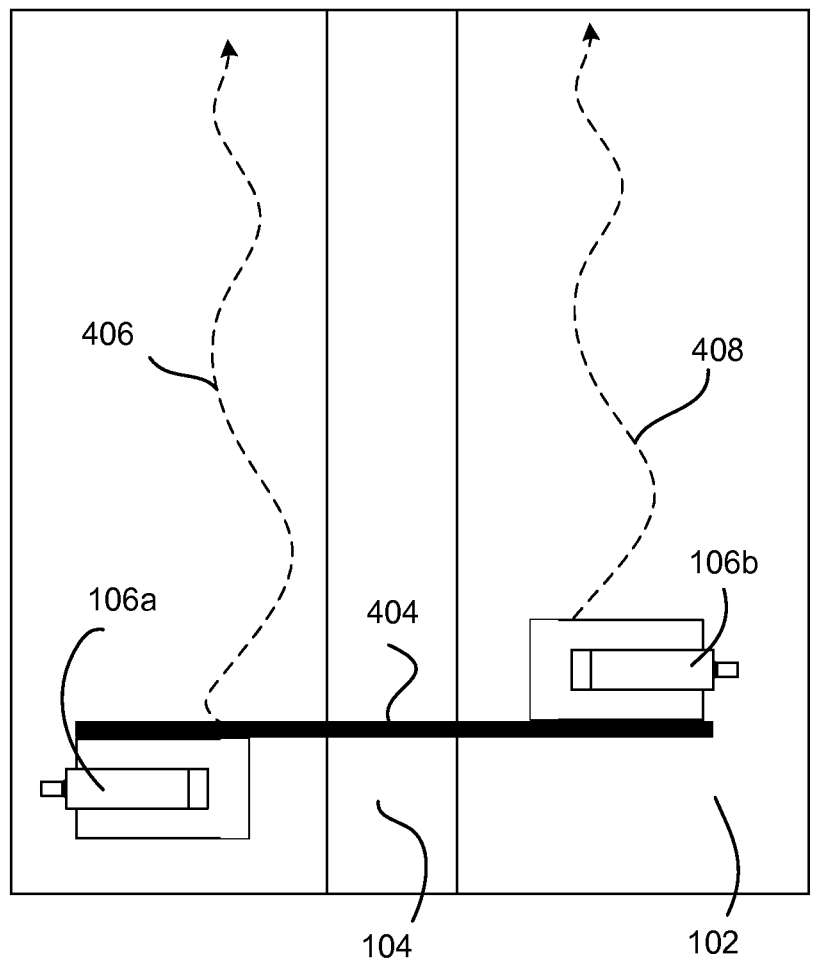
Figure 2:
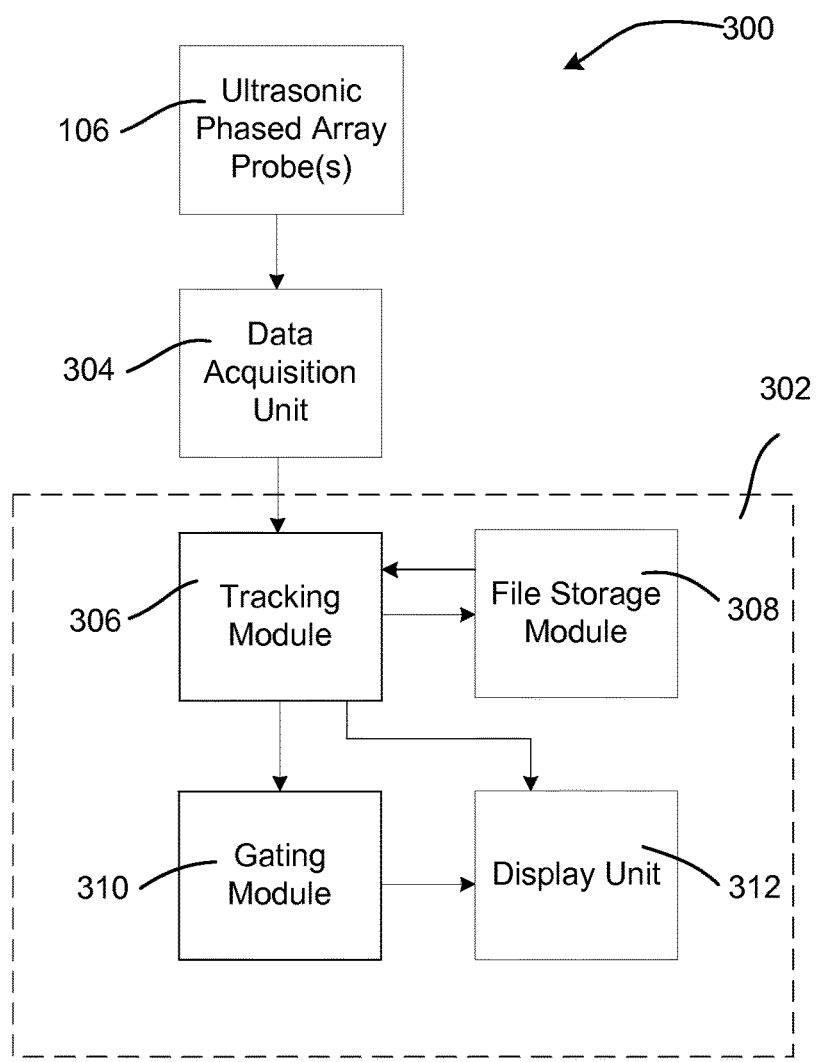
FIG. 2 is a schematic view of an NDT/NDI system with automated and optimized gating applied to the data analysis process according to the present disclosure.

Referring to FIG. 2, a phased array inspection system 300 is configured for weld inspection enabling a data analysis process with automated and optimized gating taking into account the actual distance between a phased array probe and a weld line. As can be seen in FIG. 2, system 300 comprises at least one phased array probe 106 operable to beam ultrasonic energy into a weld line, such as that of 104 in FIG. 1b, and to receive response echo and provide corresponding electronic echo signals; a data acquisition unit 304 receiving the electronic echo signals from probe 106 and sending commands to probe 106 with a predetermined focal law; a data processing and analyzing module 302 configured to process and analyze the electronic echo signals and identify an anomaly in the weld and instruct a display module 312 to display such.

Analyzing module 302 further comprises a tracking module 306 configured to produce dynamically corrected overlays of the weld line based on the echo signals, the dynamically corrected overlays having a series of offsets from the initial overlay; a gating module 310 configured to provide dynamic target gating adjusted by at least part of the offset.

More specifically, with advanced reference to FIG. 5b, tracking module 306 deduces the relative mechanical drift 820 (shown later in FIG. 5b) based on the position of geometry related echoes such as 818 (FIG. 5b) and provides a corrected distance from probe to weld center to a file storage module 308, to a display unit 312 and to gating module 310. Gating module 310 gates the phased array UT data according to the corrected distance value and allows optimized noise filtering. This yields more accurate and better visualized testing results with noise effectively filtered out by dynamic gating.

Figure 3:
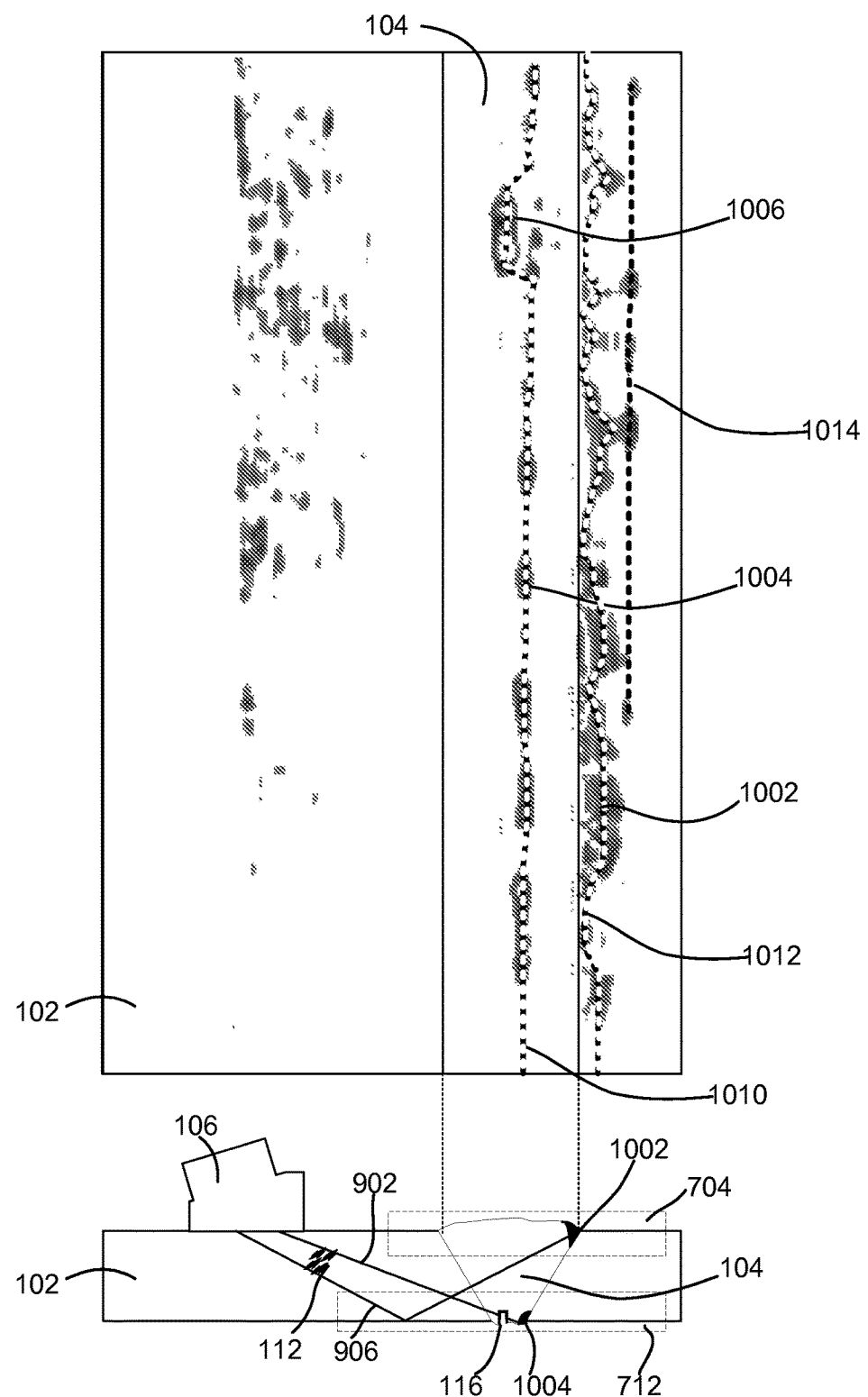
FIG. 3 is a schematic and image view of an actual PAUT signal with precise gating applied according to the present disclosure.

To explain the novel solution to the aforementioned problems, an exemplary actual PAUT scan image is presented in FIG. 3. As seen in FIG. 3, the top portion is a top view representation of the actual PAUT scan. This top view is not gated, and shows all signals over a certain threshold of the signal amplitude. Phased array probe 106 (positioned on the left side of weld 104) receives a signal that includes a plurality of beams (such as a beam 902 and a beam 906), ensuring coverage of both the cap and the root areas of the weld in the same scan. Phased array probe 106 thus receives echo signals from a cap 1002 and a root 1004, but also signals from a defect 116 and a noise echo from flaw 112.

Noise echo from flaw 112 is filtered by a 2D tracking gate 712 and a 2D tracking gate 704. A first top view representation is made to isolate echoes from weld cap 1002, and a second top view representation is made to the isolate echoes from root 1004. Echo from root 1004 is seen intermittently in the PAUT scan image, but a small drift 1006 can be identified in the upper section of the scan. This drift is in fact associated with the presence of the defect 116 in the gated area.

Therefore tracking gate 712 of the root echoes can also include defect 116, since it is within the tracking gate. The echo from cap 1002 is less consistent, and includes some noise that can be removed by the tracking gate 704. Based on this example, it is not possible to use any tracking gate information from a calculated curve 1010 or from a calculated curve 1012 to access the real probe-to-weld distance.

Continuing with FIG. 3, a novel aspect of the present disclosure is to utilize separate tracking gates that generate mechanical drift within a defined limit in order to filter out spurious information from the curves 1010 and 1012. This will create some gaps in the position of the dynamically corrected overlay. Interpolation between valid positions of tracking gates 704 and 712 can be used to fill those gaps, and the corrected probe-to-weld center value can be provided. The advantage of using separate gates is that the noise introduced by separate sources, i.e. 112 and 116, can be cancelled out since they do not appear exactly at the same waveform. This also makes it possible to enable use of other known parameters as a cross-reference, such as a fixed horizontal distance between the weld root and the weld cap, 1004 and 1002 respectively, to eliminate position data adversely affected by noise. One skilled in the art can appreciate that if separate gates were not used, noise from both root signal and cap signal could appear at the same time in one specific waveform, and therefore none of the signals could be deemed reliable to be used with cross reference to other known parameters.

In practice, geometry echoes can have multiple sources in weld cap or weld root. In order to cover such conditions, it is possible as an alternate embodiment to add an optional additional process in order to generate multiple curves such as 1012 and 1014 for each gate. The proposed method to achieve this is to use pattern movement analysis tools such as optical flow process in order to produce a trend line illustrating the general lateral movement of the probe relative to the weld. It must be understood that such a process will provide a general idea of the displacement between one scan position and the next, but it is expected that drift relative to the real position of the weld will appear and accumulate over a given scan distance. So, instead of using the trend line as absolute and reliable information, it is rather used to regroup indications of significant amplitude that have a common source within the weld geometry (e.g. the center of the cap). Each set of regrouped information is thus represented as a separate curve such as 1012 or 1014 for the remaining process. With this method, there are no practical limits on the number of curves that can be generated for each gate.

Continuing with FIG. 3, the process of using a cross correlation (a well-known signal processing tool) to evaluate the data between curves 1010 and 1012 is further explained. The cross correlation process in this case uses sliding window algorithm elements within curves 1010 and 1012 to simultaneously compare a signal over a given length at corresponding positions between the two curves. Cross correlation over a defined threshold indicates adequate reliability of the data. Mechanical drift can thus be measured at those locations by finding the best match between the overlay position and the 1010 and 1012 curves at specific scan positions.

The cross correlation process can also be adapted to operate with the different tracking curves from two or more phased array probes. By evaluating the mutual cross correlation between each individual curve, the two curves with the best cross correlation can be selected, and then compared to the pre-defined threshold. This process can then be applied with any number of probes provided they are mechanically linked within the scanner.

Figure 4A:
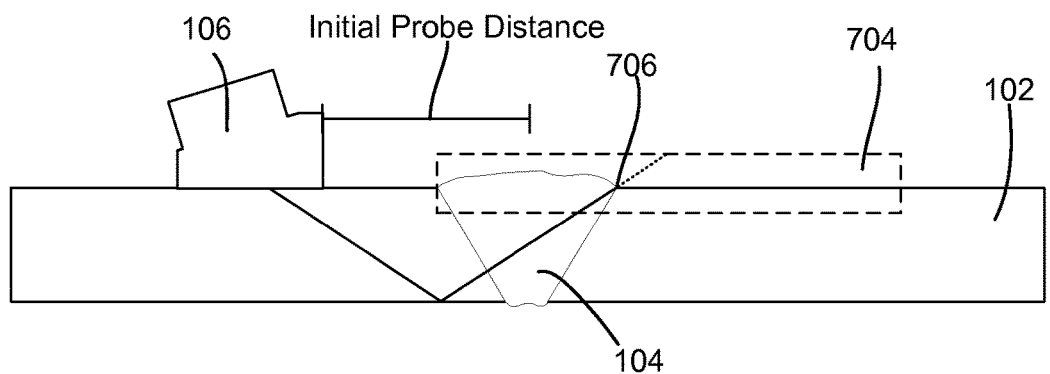
FIGS. 4a and 4b are schematic views of tracking gates with the geometrical echo tracking module that can be used to isolate geometry signals.
Figure 4B:
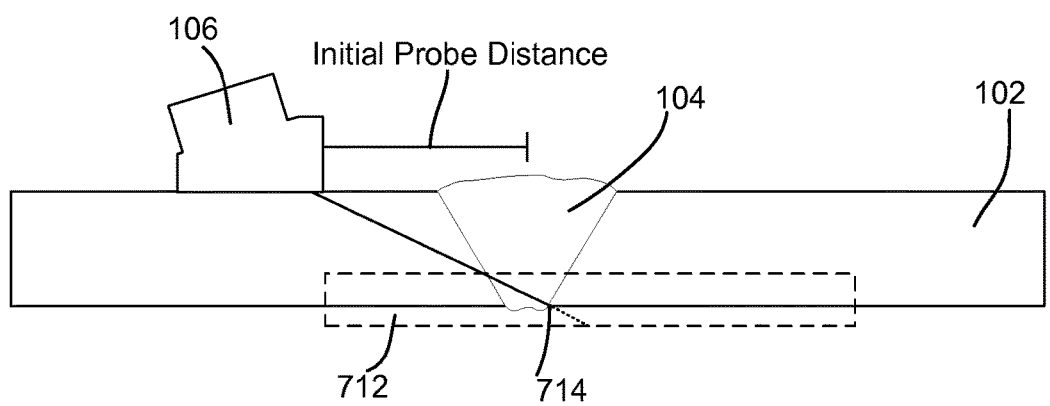

FIGS. 4a and 4b illustrate a schematic view of a way of using tracking gates 704 and 712 to enable the automatic identification of geometrical echoes in part 102. The objective is to isolate specific geometrical echoes from the noise, but also from other geometrical echoes, to enable individual tracking of echoes from various sources associated with the weld geometry.

Typically for PAUT weld inspection, echoes related to the weld geometry are generated at two specific positions for each probe, namely the weld cap and the weld root. A first position of gating is illustrated in FIG. 4a, where tracking gate 704 for a cap echo is placed relative to an initial probe distance to monitor the signal at a right cap corner 706 for a probe on the left side. A second gating position is illustrated in FIG. 4b; in this case tracking gate 712 is placed relative to the initial probe distance to monitor the signal at the right side of a root echo 714 for a probe on the left side. The output of this operation is a series of top view representations, each top view being a specific visualization of a particular geometry-related echo through the scan.

FIGS. 5a and 5b are examples of a top view representation output generated from inspection analysis with a gating arrangement shown in FIGS. 4a and 4b. FIG. 5a shows part 102 with weld 104 being inspected using phased array probe 106 at the known initial probe distance from the weld centerline. However some mechanical drift occurs, and the scan path follows scan line 406, which offsets geometrical echoes 818 from an initial weld overlay with mechanical drifts shown in FIG. 5b.

Because the geometrical echoes 818 in FIG. 5b draw a relatively continuous curve, it is possible to use an existing curve tracking algorithm (such as tracking the geometrical center of the signal at each scan position) to find a mechanical drift and dynamically correct the probe to the weld distance. By using the technique disclosed associated with FIG. 3, including separate gating and using cross-reference to identify centroids of echoes 818, a part overlay and a weld overlay are dynamically corrected along the scan axis to match positions of the tracked geometrical echo 818 on the initial weld overlay.

Tracking gates for defect detection are also corrected accordingly. It is worth mentioning that while 2D gates for defect detection are always corrected to perfectly match a dynamically corrected weld overlay position, the tracking gate may be either positioned relative to the initial probe distance or to the dynamically corrected weld overlay position.

Figure 6A:
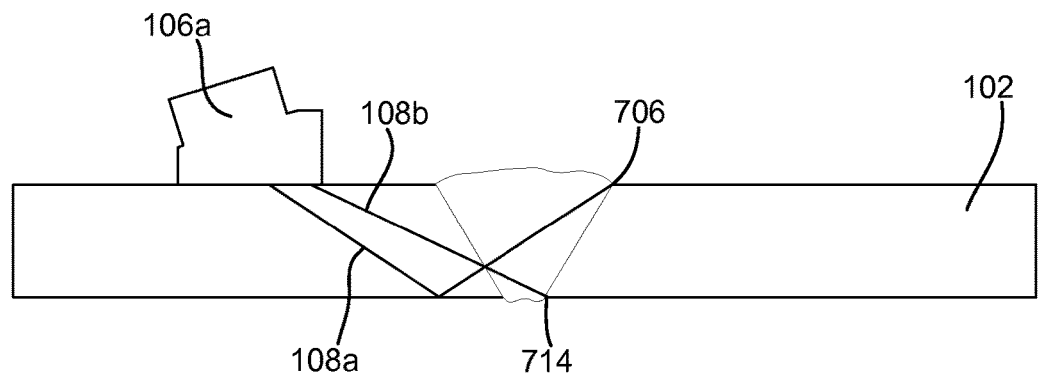
FIGS. 6a and 6b are schematic views of multiple echoes that can be used to correlate probe signals, and allow at least two phased array probes that are mechanically linked within a scanner to work together.
Figure 6B:
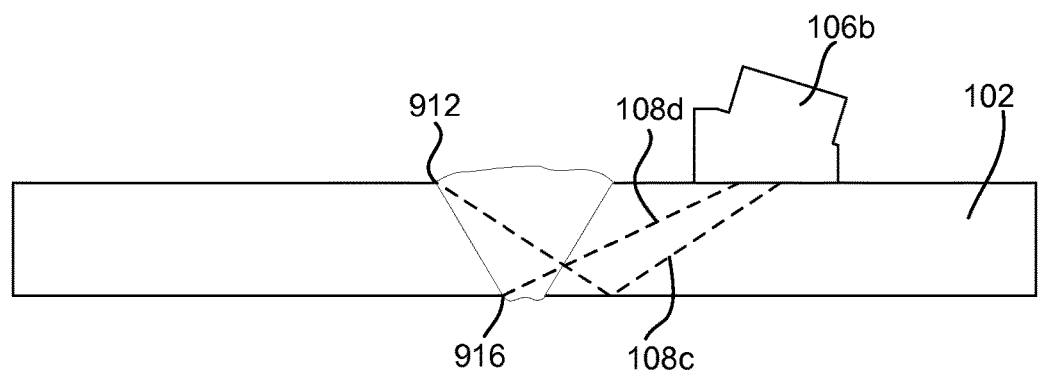

FIGS. 6a and 6b are schematic views showing geometrical echo relations permitting the combined analysis of multiple echoes due to dynamically corrected weld overlays. FIG. 6a shows phased array probe 106a inspecting part 102, targeting the cap echo 706 with an ultrasonic beam 108a and the root echo 714 with an ultrasonic beam 108b. FIG. 6b shows phased array probe 106b inspecting flat part 102, targeting cap echo 912 with ultrasonic beam 108c and root echo 916 with beam 108d. It should be understood that the aforementioned principle should readily be applied to the use of multiple probes and therefore to multiple sources of echoes, which should be within the scope of the present disclosure. Identification of weld position according to instantly or previously acquired PAUT data and subsequently applying dynamic gating should also be applied to this dual probe setup.

All those echoes can be compared to each other since they are physically linked together by scanner 404. The drift of each probe is coherent with the drift of the other; using such a scanner with two probes provides four different tracking curves that can be generated (or more using the alternate embodiment presented in [0042]. As a result, mechanical drift from the various curves measured to be within a given limit (example: three out of four curves) can be applied in order to assess valid measurements that consider all the curves, or a fraction of all the curves. This process can then be applied with any number of probes provided they are mechanically linked within the scanner. Alternatively, the cross correlation process can also be adapted to operate with those four curves by evaluating the mutual cross correlation between each individual curve then selecting the two curves with the best cross correlation (which is then compared to the pre-defined threshold). Of course, this principle can then be applied with any number of probes provided they are mechanically linked within a scanner.

Figures 7A, 7B:
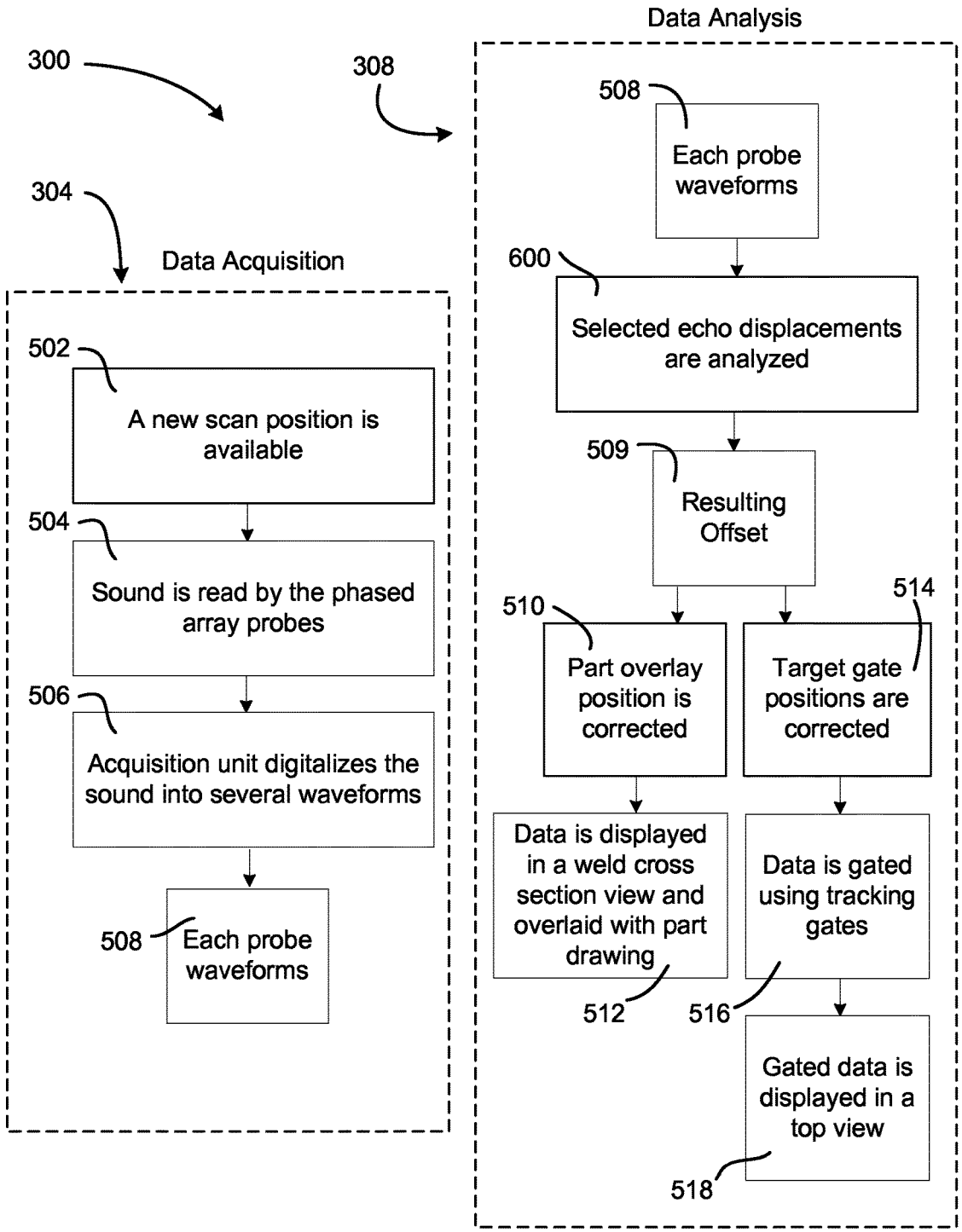
FIGS. 7a and 7b are flow charts showing the steps of automating and optimizing gating applied to the data analysis process according to the present disclosure.

Reference now is made to FIGS. 7a and 7b, which provide summarized steps encompassing the aforementioned solutions that can be executed by data processing and analyzing unit 302 in FIG. 2. FIGS. 7a and 7b elaborate steps of a process of automated measurement of the distance between the phased array probe and a predetermined geometric characteristic of the weld surface, such as one of the weld caps. More particularly, FIG. 7a shows the detailed steps related to the operation of data acquisition unit 304; FIG. 7b shows the detailed steps executed in the file storage module 308.

Referring now to FIG. 7a, phased array probe 106 reads the PAUT signal, and then sends the signal to data acquisition unit 304. At step 502, the PAUT signal is sent from probe 106 for each new scan position as probe 106 moves along the weld line. At step 504 the PAUT signal is read and in step 506 it is digitized. At step 508, phased array probe 106 produces several waveforms for each scan position. Before proceeding to FIG. 7b, reference is made to FIG. 8 to elaborate the steps leading to step 509 in FIG. 7b for determining the resulting offset of the actual weld line.

Figure 8:
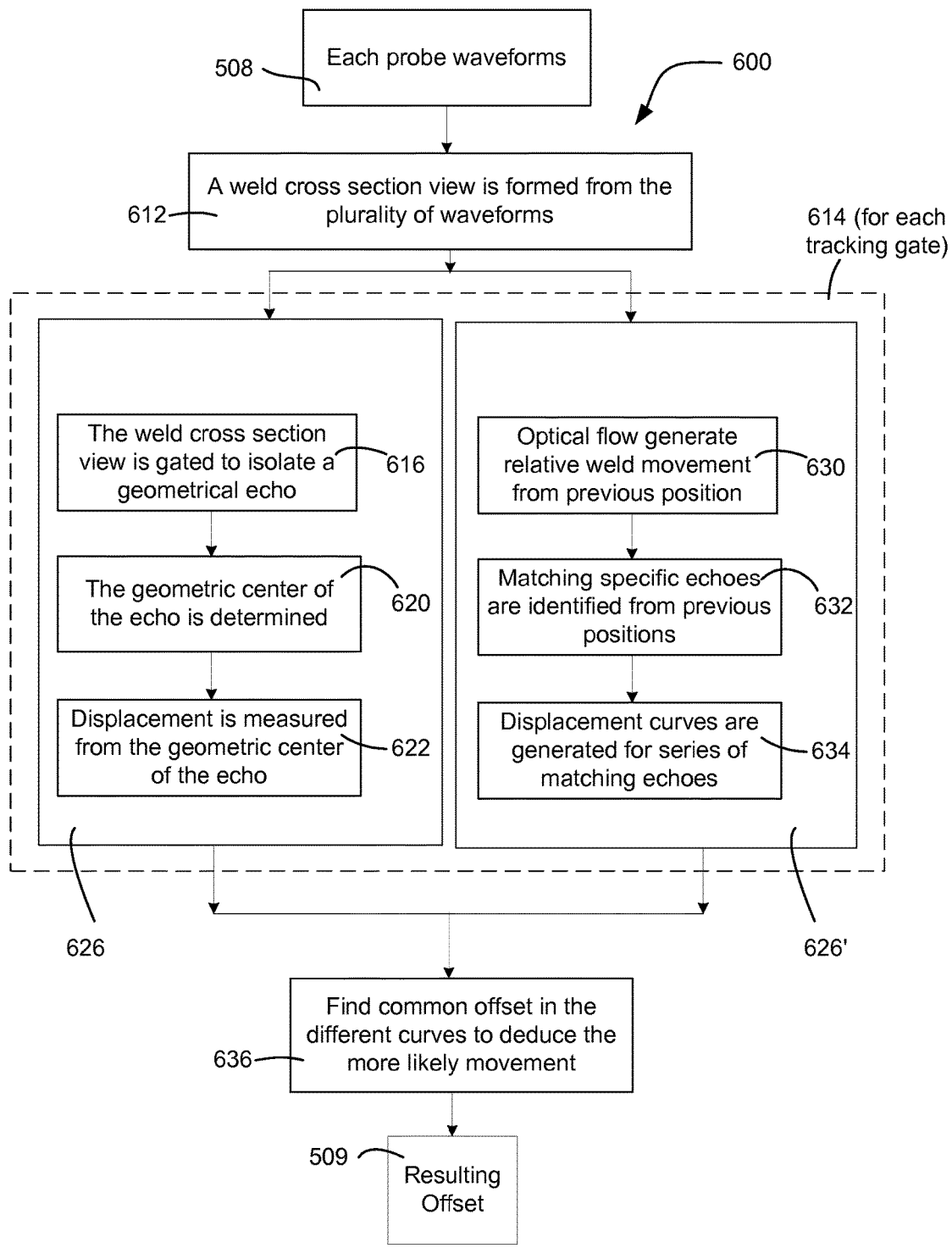
FIG. 8 is a flow chart detailing the steps of automating and optimizing the gating method applied to a data analysis process in which the measurement position between the phased array probe and the weld surface is automated by means of a geometrical echo tracking module.

FIG. 8 elaborates on a process 600 enabling the automated measurement of the distance between the phased array probe and the weld surface for the preferred embodiment. For each tracking gate in the phased array probe, independent processes for generating the weld cross section views from step 612 are simultaneously performed through step 614. This step further includes one of the two groups of three sub-steps, 626 or 626'. First, in 626, step 616, a specific tracking gate is applied on the PAUT signal to isolate its geometrical echo. In step 620, a gated weld cross section view 616 is analyzed and the center of the geometrical echo is found. In step 622 a displacement is then measured based on the geometric center position of the tracking gate relative to the expected position of the geometrical center of the echo.

It should be noted that the geometric center of the echo, namely the echo from the center of one of the weld caps, is used as the exemplary embodiment. It should be understood that employing other geometric features, such as the center of one the weld roots of a weld, should be within the scope of the present disclosure.

Similarly and optional to process 626, as shown in optional process 626' the automatic measurement of displacement can be determined by geometry echoes at multiple distinct positions in the weld cap. First, in step 630 an optical flow pattern movement tracking generates a trend line representative of the lateral probe movement of the scanner during the inspection. In step 632, sets of echoes at position matching the relative movement pattern are regrouped. In step 634, displacement curves are generated for each set of regrouped echoes. It should be noted that optical flow pattern recognition is a widely known image recognition method.

Continuing with FIG. 8, in step 636, the resulting offsets from each of the displacement curves are analyzed to find a common (or similar) offset. If applicable, relevant displacement information is kept; otherwise interpolation to the adjacent position is used to fill the gap. The result of step 600 is an offset 509, which is used to calculate the position of the dynamically corrected weld overlay.

With the resulting offset denoting a displacement according to the PAUT data at the specific scan location, reference is made back to FIG. 7b. As shown in FIG. 7b, analyzing unit 308 analyzes the waveform from step 508 previously acquired during data acquisition or from existing post-acquisition. At step 600, the digitized displacement of the different echoes in the selected tracking gates are analyzed. At step 510, the part overlay and the new position of the weld overlay are calculated according to the resulting offset 509 shown in FIG. 8. At step 512, the phased array probe waveforms from step 508 are mapped in a weld cross section view, where every waveform is corrected using its theoretical position in part 102. The weld cross section view data is then dynamically displayed overlaid with the part overlay and the weld overlay. At step 514, preferably simultaneously with steps 510 and 512, the initial target gate positions are corrected according to the resulting displacement offset 509 that is the result of step 600. The top view data is then gated at step 516 and displayed at step 518, with the gating position automatically adjusted with the corrected distance between phased array probe 106 and weld 104.

It should be noted and appreciated the correction of part overlay herein disclosed directs to the correction of relative displacement from a pre-determined characteristic of the echo, such as the center of an echo. Similarly to correcting by moving the gate, one skilled in the art can achieve such correction instead by moving the assumed location associated with the data of the echoes. Such approach is also within the scope of the present disclosure.

Although the present invention has been described in relation to particular exemplary embodiments thereof, many other variations and modifications and other uses will become apparent to those skilled in the art. It is preferred, therefore, that the present invention not be limited by the specific disclosure.

What is claimed is:

1. A non-destructive testing and inspection (NDT/NDI) device operable to conduct an NDT/NDI test operation on a weld of a test object, the weld forming a weld line, and the device having an initial overlay of the cross section of the weld and an initial scan path along the weld line,
the NDT/NDI device comprising:
at least one phased array probe operable to beam ultrasonic energy into and along the weld line, receive response echoes and provide corresponding sets of electronic echo signals, with each set of the electronic echo signals corresponding to a scan path location;
a data acquisition unit receiving the electronic echo signals from the at least one probe and sending commands to the probe with predetermined focal law;
a data processing and analyzing module configured to process and analyze the electronic echo signals and identify an anomaly in the weld and instruct a display module to display such, the analyzing module further comprising,
a tracking module configured to produce dynamically corrected overlays of the weld line based on the echo signals, the dynamically corrected overlays having a series of offsets from the initial overlay;
a gating module configured to purposefully determine the relative positions of a plurality of data analysis gates to filter out noise caused by sources unrelated to the weld, and to provide dynamic target gating adjusted by at least part of the offset.

2. The NDT/NDI device in claim 1 further comprising an electronic memory for storing data related to the echo signals, wherein the analyzing module is configured to perform analysis during the test operation or post the test operation using data stored in the memory.

3. The NDT/NDI device in claim 1, wherein said tracking module is configured to acquire data from the data acquisition unit during the test operation.

4. The NDT/NDI device in claim 1 having two or more phased array probes that are mechanically and rigidly linked.

5. The NDT/NDI device in claim 1, wherein the initial overlay and the corrected overlay include at least one corresponding predetermined geometric characteristic of the weld.

6. The NDT/NDI device in claim 5, wherein the at least one geometric characteristic of the weld is a weld cap or a weld root.

7. The NDT/NDI device in claim 5, wherein the data acquisition unit is configured to operate in a plurality of acquisition cycles, each of which corresponds to one set of ultrasonic echo signals indicating an axial position along the initial scan path.

8. The NDT/NDI device in claim 7, wherein the tracking module is configured to identify the position of the at least one geometric characteristic obtained from a specific set of echo signals in a coordinate formed by the initial scan path and its transversal line.

9. The NDT/NDI device in claim 7 wherein the position of the echo signal is the centroid of each echo signal corresponding to the characteristics on the weld line.

10. The NDT/NDI device in claim 8, wherein the at least one geometric characteristic includes at least two geometric characteristics, and there is a known and constant geometric relationship between the at least two geometric characteristics.

11. The NDT/NDI device in claim 10, wherein the constant geometric relationship is a constant distance between the two geometric characteristics corresponding to the set specific set of the echo signals.

12. The NDT/NDI device in claim 9, wherein the tracking module is configured to use the constant geometric relationship as a reference value to confirm and/or correct the position of the echo signal corresponding to the geometric characteristics.

13. The NDT/NDI device in claim 5, wherein the gating module uses separate and individual gates for each of the at least one geometric characteristics.

14. The NDT/NDI device in claim 1, wherein said gating module correlates and overlays ultrasonic scanning data to automatically adjust readings from the phased array probes.

15. The system and method in claim 1, wherein said display unit can display the automatically adjusted readings from the phased array probes to accurately measure ultrasonic scan distances on welds, parts and overlays.

16. A method of abating noise from sources non-related to a weld during a non-destructive testing and inspection (NDT/NDI) on the weld using at least one phased array probe, the weld forming a weld line, and the device having an initial overlay of the weld and an initial scan path,
the method comprising the steps of:
beaming ultrasonic energy into the weld while moving the probe along the weld line, receiving response echoes and providing corresponding sets of electronic echo signals, with each set of electronic echo signals corresponding to a location along the scan path location;
receiving the electronic echo signals from the probe and sending commands to the probe with predetermined focal law;
producing a location of a specific set of the echo signals defined by its longitudinal and transversal positions relative to the scan path;
calculating an offset between the location of the specific set of the echo signals in comparison to its corresponding position on the initial scan path;
deducing a corrected weld overlay based on the offset;
applying dynamic gating based on the corrected weld overlay for the location;
conducting data processing and analysis utilizing the dynamic gating.

17. The method of claim 16, wherein the step of calculating the offset and deducing the corrected weld overlay is performed by a tracking module, and,
the step of applying dynamic gating is performed by a gating module.

18. The method of claim 16, wherein the step of identifying the location of the specific set of the echo signals comprises identifying the geometric center of a geometric characteristic of the set of the echo signals.

19. The method of claim 16, wherein the step of identifying the location of the specific set of the echo signals comprises identifying two or more distinct geometric characteristics the set of the echo signals by using pattern recognition method.

20. The method of claim 18, wherein the geometric characteristic is a weld cap or weld root.

21. The method of claim 18, wherein the dynamic gating is to position a plurality of data analysis gates to abate the noise caused by sources unrelated to the weld, and to provide dynamic target gating adjusted by at least part of the offset so that the data processing and analysis can analyze the electronic echo signals with the abated noise and identify an anomaly in the weld.

* * * * *